(12) United States Patent  
Herzenberg et al.

(10) Patent No.: US 7,650,351 B2
(45) Date of Patent: Jan. 19, 2010

(54) INTERNET-LINKED SYSTEM FOR DIRECTORY PROTOCOL BASED DATA STORAGE, RETRIEVAL AND ANALYSIS

(76) Inventors: Leonard A. Herzenberg, 876 Cedro Way, Stanford, CA (US) 94305; David Rhodes Parks, 686 Cherry St., San Francisco, CA (US) 94131; Leonore A. Herzenberg, 876 Cedro Way, Stanford, CA (US) 94305; Wayne A. Moore, 4308 19th St., San Francisco, CA (US) 94114; Vernon T Oi, 1259 Marilyn Ct., Mountian View, CA (US) 94040

( * ) Notice: Subject to any disclaimer, the term of this patent is extended or adjusted under 35 U.S.C. 154(b) by 302 days.

(21) Appl. No.: 11/194,964

(22) Filed: Aug. 2, 2005

(65) Prior Publication Data

US 2005/0273475 A1    Dec. 8, 2005

Related U.S. Application Data

(63) Continuation of application No. 09/860,222, filed on May 18, 2001, now Pat. No. 6,947,953, and a continuation-in-part of application No. 09/434,240, filed on Nov. 5, 1999, now abandoned.

(60) Provisional application No. 60/205,489, filed on May 19, 2000.

(51) Int. Cl.
 *G06F 17/30* (2006.01)
(52) U.S. Cl. ............................. 707/101; 707/3; 707/10; 707/102
(58) Field of Classification Search ........................ None
See application file for complete search history.

(56) References Cited

U.S. PATENT DOCUMENTS 5,594,529 A    1/1997    Yamashita et al. .............. 399/8
5,612,357 A *  3/1997    Keenan et al. .............. 514/343

(Continued)

FOREIGN PATENT DOCUMENTS

WO    WO 00/28437    *    5/2000

(Continued)

OTHER PUBLICATIONS

Gonzalez-Couto, et al., "The Life Science Global Image Database (GID)", Nucleic Acids Research, Jan. 1, 2001, Oxford University Press, <http://pubmedcentral.nih.gov/articlerender.fcgi?artid=29843>, Retrieved Sep. 22, 2007, p. 1-7.*

(Continued)

*Primary Examiner*—Khanh B Pham
(74) *Attorney, Agent, or Firm*—Greenberg, Traurig, LLP (57) ABSTRACT

The present invention is related to databases and the exchange of scientific information. Specifically the invention disclosed a unified scientific database that allows researchers to easily share their data with other researches. The present invention also allows for the ease of data collection, annotation, storage, management, retrieval and analysis of scientific data through and into the database. In addition, it allows for archival storage and retrieval of data collected directly from laboratory instruments to ensure data consistency for patent and other purposes. It also allows for ease of sharing data between laboratories in remote locations. The present invention also supports the automated creation of experimental protocols.

7 Claims, 5 Drawing Sheets

U.S. PATENT DOCUMENTS

| | | | | |
|---|---|---|---|---|
| 5,937,364 | A | * | 8/1999 | Westgard et al. ............... 705/7 |
| 5,958,670 | A | * | 9/1999 | Goodrich et al. ............... 435/2 |
| 5,970,490 | A | | 10/1999 | Morgenstern ................ 707/10 |
| 5,983,234 | A | * | 11/1999 | Tietjen et al. ........... 707/103 R |
| 5,995,937 | A | | 11/1999 | DeBusk et al. ................. 705/2 |
| 6,063,028 | A | | 5/2000 | Luciano ...................... 600/300 |
| 6,097,995 | A | * | 8/2000 | Tipton et al. ................. 700/266 |
| 6,098,062 | A | | 8/2000 | Janssen ....................... 706/59 |
| 6,154,738 | A | * | 11/2000 | Call ............................. 707/4 |
| 6,169,981 | B1 | | 1/2001 | Werbos ....................... 706/23 |
| 6,249,883 | B1 | | 6/2001 | Cassidy et al. ................ 714/42 |
| 6,263,330 | B1 | | 7/2001 | Bessette ....................... 707/4 |
| 6,314,361 | B1 | * | 11/2001 | Yu et al. ........................ 705/5 |
| 6,326,147 | B1 | * | 12/2001 | Oldham et al. ................. 435/6 |
| 6,366,954 | B1 | | 4/2002 | Traversat et al. ............ 709/220 |
| 6,387,907 | B1 | * | 5/2002 | Hendricks et al. ...... 514/254.06 |
| 6,480,748 | B1 | | 11/2002 | Gerszberg et al. ............. 700/21 |
| 6,489,168 | B1 | * | 12/2002 | Wang et al. ................. 700/268 |
| 6,510,350 | B1 | | 1/2003 | Steen et al. .................... 700/9 |
| 6,581,012 | B1 | * | 6/2003 | Aryev et al. ................... 705/2 |
| 6,581,038 | B1 | * | 6/2003 | Mahran ...................... 707/101 |
| 6,654,736 | B1 | * | 11/2003 | Ellis et al. ...................... 707/3 |
| 6,675,166 | B2 | * | 1/2004 | Bova ........................... 707/10 |
| 6,678,703 | B2 | * | 1/2004 | Rothschild et al. .......... 707/201 |
| 6,766,322 | B1 | * | 7/2004 | Bell ............................ 707/10 |
| 6,909,974 | B2 | * | 6/2005 | Yung et al. .................... 702/31 |
| 7,217,509 | B2 | * | 5/2007 | Wolffe et al. ................... 435/6 |
| 7,319,976 | B1 | * | 1/2008 | Peckover ..................... 705/14 |
| 2002/0019751 | A1 | * | 2/2002 | Rothschild et al. ............. 705/3 |
| 2003/0036683 | A1 | * | 2/2003 | Kehr et al. .................. 600/300 |

FOREIGN PATENT DOCUMENTS

WO             01/16375            11/2001

OTHER PUBLICATIONS www.limsource.com, "What's New Right Now", Jan. 10, 1997, <Retrieved from archive.org on May 25, 2008 http://web.archive.org/web/19970110144104/http://www.limsource.com/whatnew/indnews/11to1296.html>.*

Kirkpatrick, "Handbook for Cinical Trials", Dec. 1998, Taylor and Francis, First Ed., P. cover, copyright, 7-10, 10, 19, 47-49, <Retrieved from Amazon.com on Jan. 4, 2008>.*

Ben-Basat M. et al, "A Hierarchical Modular Design for Treatment Protocols", Dialog, Embase, Dec. 1980, XP 002913397, p. 1 (abstract) <Retrieved from eDAN>.*

Good, The LDAP Data Interchange Format (LDIF)—Technical Specification <draf-good-ldap-ldif-05.tex>, IDTF Draft, online, Oct. 16, 1999, p. 1-16.*

Moore, Wayne A.; "A Directory Of Biological Materials".

Ben-Basat M. et al, "A Hierarchical Modular Design for Treatment Protocols", Dialog, Embase, 1980, XP002913397.

Grant Proposal for IBRSS System, pp. 1-17.

* cited by examiner

INTERNET-LINKED SYSTEM FOR DIRECTORY PROTOCOL BASED DATA STORAGE, RETRIEVAL AND ANALYSIS

SUMMARY

This application is a Continuation of U.S. application Ser. No. 09/860,222 filed May 18, 2001 now U.S. Pat. No. 6,947,953, which claims the benefit of U.S. Provisional Application No. 60/205,489 filed May 19, 2000. The application is also a Continuation-In-Part of U.S. application Ser. No. 09/434,240, filed November 5, 1999 now abandoned. The present invention is related to databases and the exchange of scientific information. Specifically the invention disclosed a unified scientific database (IBRSS) that allows researchers to easily share their data with other researchers. The present invention also allows for the ease of data collection, annotation, storage, management, retrieval and analysis of scientific data through and into the database. In addition, it allows for archival storage and retrieval of data collected directly from laboratory instruments to ensure data consistency for patent and other purposes. It also allows for ease of sharing data between laboratories in remote locations. The present invention also supports the automated creation of experimental protocols.

BACKGROUND

I. Fluorescent Activated Cell Sorting (FACS)

Flow cytometry is a technique for obtaining information about cells and cellular processes by allowing a thin stream of a single cell suspension to "flow" through one or more laser beams and measuring the resulting light scatter and emitted fluorescence. Since there are many useful ways of rendering cells fluorescent, it is a widely applicable technique and is very important in basic and clinical science, especially immunology. Its importance is increased by the fact that it is also possible to sort fluorescent labeled live cells for functional studies with an instrument called the Fluorescence Activated Cell Sorter (FACS).

Flow cytometry has always been computerized because without computers the data analysis would be infeasible. As flow cytometry has matured, the importance of combining flow data with data from other sources has become clear, as has the need for multi site collaborations, particularly for clinical research. This lead to our interest in developing methods for naming or identifying flow cytometry samples, reagents and instruments (among other things) and in maintaining a shared repository of information about the samples etc.

Flow cytometry was revolutionized in the late 1970s with the introduction of monoclonal antibodies that could be coupled to a fluorochrome and used as FACS reagents. However, nomenclature for these reagents has been a hodgepodge, in spite of the fact that monoclonals are useful precisely because they can be uniquely and accurately named, i.e., the antibody produced by a clone is always the same whereas naturally produced sera are highly variable. Our work in capturing the experimental semantics of FACS experiments made it clear that we needed at least a local nomenclature and underscored the value of a global nomenclature for FACS data and monoclonal antibodies, which are useful in many fields beside flow cytometry.

II. DNA Arrays

During the past decade, the development of array-based hybridization technology has received great attention. This high throughput method, in which hundreds to thousands of polynucleotide probes immobilized on a solid surface are hybridized to target nucleic acids to gain sequence and function information, has brought economical incentives to many applications. See, e.g., McKenzie, et al., *Eur. J. of Hum. Genet.* 6:417-429 (1998), Green et al., *Curr. Opin. in Chem. Biol.* 2:404-410 (1998), and Gerhold et al., *TIBS,* 24:168-173 (1999).

III. Gels

Gel electrophoresis is a standard technique used in biology. It is designed to allow sample to be pulled through a semisolid medium such as agar by an electromagnetic force. This technique allows for separation of small and macromolecules by either their size or charge.

IV. Prior Art

Although there are wide variety of tools that purport to help scientists deal with the complex data collected in today's laboratories, virtually all of these so-called Laboratory Information Systems (LIMS) or Electronic Laboratory Notebook systems (ELNs) approach data collection and management from the perspective of final data output and interpretation. None of these systems addresses the basic needs of the bench scientist, who lacks even minimal tools for automating the collection and storage of data annotated with sufficient information to enable its analysis and interpretation as a study proceeds.

The absence of automated support for this basic laboratory function, particularly when data is collected with today's complex data-intensive instrumentation, constitutes a significant block to creative and cost-effective research. Except in very rare instances, the study and experiment descriptions that scientists need to interpret the digitized data these instruments generate are stored in paper-bound notebooks or unstructured computer files whose connection to the data must be manually established and maintained. The volatility of these connections, aggravated by turnover in laboratory personnel, makes it necessary to complete the interpretation of digitized data as rapidly as possible and seriously shortens the useful lifetime of data that could otherwise be mined repeatedly.

In addition, because paper notebook or unstructured computer information is difficult to make available to other investigators, particularly at different sites or across time, laboratories that would like to make their primary data or their specific findings available to collaborators or other interested parties are unable to do so. Thus, although computer use now facilitates many aspects of research, and although the Internet now makes data sharing and cooperative research possible, researchers are prevented from taking full advantage of these tools by the lack of appropriately tailored computer support for integrating and accessing their work.

Finally, because the minimal computerized support for research that currently exists has developed piecemeal, usually in response to needs encountered during collection of particular kinds of data, no support currently exists for providing lateral support to integrate different types of data collected within an overall study. For example, although automated methods for collecting, maintaining and using DNA microarray data are now becoming quite sophisticated, the integration of these data with information about the source of the material analyzed, or with data or results from FACS or other types analyses done with the same material, is largely a manual task requiring recovery of data and information stored on paper or in diverse files at diverse locations that are often known only to one or a small number of researchers directly concerned with the details of the project. In fact, it is common for individual bench scientists to repeat experiments sometimes several times because key information or data was "misplaced" or its location lost over time.

DETAILED DESCRIPTION

The present invention will be best understood from the point of view of a laboratory worker using the invention. The invention may allow the user to simplify laboratory work by allowing interactive automation of much of the work with the use of a computer. The work that may be performed by the present invention may be able to make the researcher more efficient. The steps of the laboratory process the invention may address is collecting, sharing, retrieving, analyzing, and annotating data. Although the present invention has equal application to the storage of any data type, one embodiment relates to the storage of data associated with a biological sample data.

Figure 5:
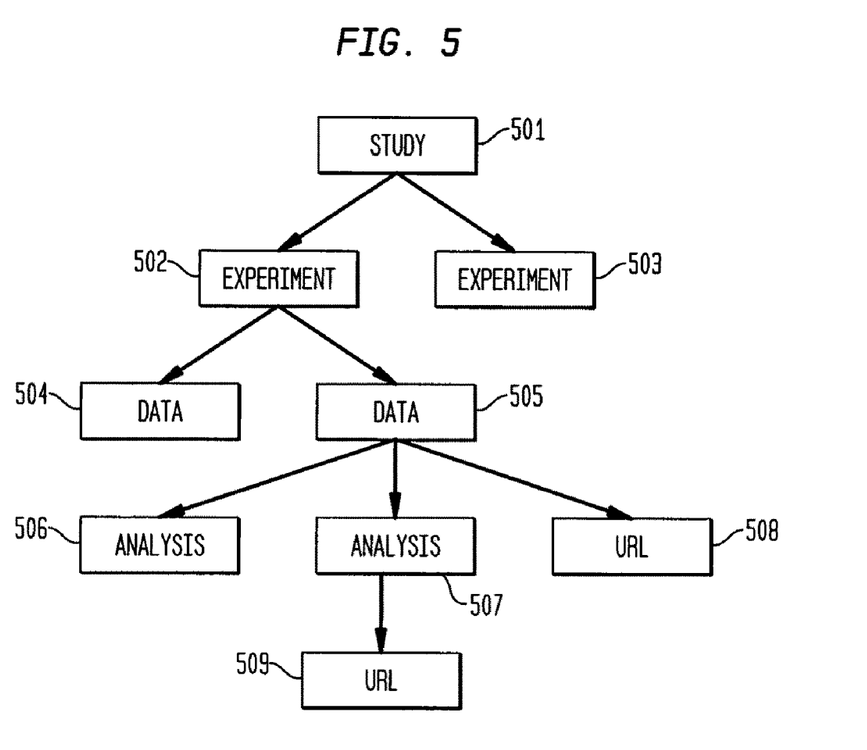
FIG. 5 is an example of a hierarchical structure of a single study.

Referring to FIG. 5, the first step the researcher may perform is to define a study 501. A study may be defined as the overall goal of the research the researcher may wish to attain. In the normal course of science a researcher creates experiments to perform the research in the study. The study may contain protocols that capture the hypothesis to be tested and the factors that go into them, including subjects, treatments, experiments, samples and the study timeline. In addition, the study may contain data and information collected in experiments that are part of the study. This may create a parent study node under which information and data pertaining to the study may be kept in child nodes.

The present invention may allow a researcher to create experiments and experimental protocols 502 and 503 that may become part of the overall study. The experiment may contain protocols that acquire information to define the subset of subjects for which the data may be collected, the set of samples to be obtained from the subjects, and the analytic procedures and data collection instruments used to analyze the samples. The experiment protocol may become a child node of its parent study.

As a typical researcher does today, the researcher using the present invention also may obtain data 504 and 505 for each study and experiment he performs. The data may be collected each time the researcher performs the same experiment protocol. The data may also contain protocols designed to acquire annotation information to define the subdivision (aliquotting) and the treatment (reagents and conditions) for a set of samples for which data may be collected by a single analytical method (usually a single instrument). Researchers then analyze data they obtain, and the researcher using the present invention may analyze the collected data. This analysis may be stored as a child-node of the data or the annotation of the data 506 and 507.

When the analysis is complete, the present invention may create Internet addresses for all of the results of the individual analyses and for the data sets created. These may be child nodes 508 and 509 of the data or experiment information. Thus, the present invention allows the user to possess unique web addresses for any of the data or analysis results that he may wish to include in a publication. The study, experimental protocol, data collection, and analysis results, may be stored as described in FIG. 5.

The study and the experiment are still the touchstone of research science. The present invention may allow the researcher to interactively create protocols for studies and experiments. The protocol creators may use wizards to ease the researcher's creation of the protocols. The researcher may invoke a protocol creator/editor on a computer. The computer may provide the researcher with a list of possible studies or experiments the researcher may wish to perform. The computer may also provide the ability for the researcher to create an entirely new type of study or experiment. After the type of study or experiment is chosen, the researcher may then be a given the option of how to set up the experiment.

Several types of possible studies, experiments and options are listed here, however the person ordinarily skilled in the art will realize how to put other types of experiments into the present invention. The types of experiments that will be described in this application specifically are clinical and basic studies and FACS and electrophoresis gel experiments. Other types of data that can be similarly stored and used within the database include DNA microarray data and clinical data. The clinical data may include red blood cell counts and RBC, MCV, MHC, MCHC, and potassium levels or may include observational data such as blood pressure, temperature, types of drugs taken, race, age, etc.

An example of a study may be a clinical study. The study may be designed to test one or more hypotheses. An example of a hypothesis may be testing whether the number of CD8 T cells is correlated with the erythrocyte volume.

In the study, HIV-infected patients may be recruited on the basis of meeting a series of entry criteria. Examples of such criteria are:

1) information collected directly by interviewing the patient 2) results of clinical analyses such as erythrocyte counts 3) results of FACS analyses such as number of CD4 T cells Experiments in the study may be conducted on samples from patients to determine whether the patient meets the entry criteria for the study. In this case, information and experiment results for each potential study entrant may be stored in the study. The study may contain experiments such as staining cells from the patients with antibodies that reveal cells that express surface CD4 and analyses such as those that enumerate the number of cells expressing CD4. Relevant information about the subjects (patients) in the study may be passed from the study to protocol wizards that may help the user define the contents of experiments such as which samples from which subjects may be examined. The study may also allow the user to select from model protocols for the experiment to define types and the amounts of the FACS reagents that may be used. For example, once information for a subject is entered into the study, the study subject may appear on a list from which the user chooses the samples to be examined in an experiment.

The study may also specify that the protocol automatically send data that is collected to analysis programs and provide necessary information to enable the automated analysis and to return specified results of the analysis to the study. Similarly, when these data are returned, the study may be triggered to specify automated analyses that return further digested results to the study. One result of this process may be the automatic identification of subjects that qualify for further study by determining that the study criteria are met, such as the subjects' erythrocyte counts and CD4 counts are within the specified ranges. Further, the automated analysis may include the returning of FACS plots comparing CD4 and CD8 levels, the returning of charts with each subject's mean levels of CD4, CD8, erythrocyte counts, or other specified variables. The automated analyses may also specify the performance of statistical procedures and the return of results of these analyses. In addition, the study may have methods for summarizing and displaying results of analyses. Finally, the study may track samples to determine whether required experiments were performed and specified data returned and may contain information about the physical location of stored samples, the amount of the sample that has been used, the treatment of the sample.

A basic research study may contain samples from mice, information about the genetic makeup of the mice and references to other genome databases relevant to the mice. It may also contain information about the treatments that individual or groups of mice were given or may be given during the experiment and about the drugs or other materials with which the mice were or may be treated. The study may also contain the timeline for treatment and, as above, define protocols and automated analyses for collected data.

A FACS experiment in a study comprises staining cells with various fluorescent antibodies and running and possibly collecting cells through a cell sorter. The wizard may help the experimenter create his experiment by creating a suggested protocol for him to follow. The wizard or other interactive device may ask the researcher how many different stains he wishes to use to mark various structures. These stains may, but do not necessarily need to be stains for different structures. Typically the stains may be fluorescent conjugated antibodies. The user may then inform the protocol creator which structures he wishes the stains to mark and the wizard may respond with an offer of a series of "option" lists from which the user may select the type of cells and the specific reagents to be used in the experiment. Option lists may be generic types of cells or cells and samples specified in the parent study to which the experiment belongs.

The wizard then may ask the researcher which FACS machine he plans to use. Each FACS machine may be equipped with different lasers or light filters enabling different FACS machines to collect data for antibodies labeled with different fluorescence "colors". The wizard may then determine whether the FACS machine specified by the user is able to take data for the fluorescent reagents selected in the protocol. Alternatively, the wizard my suggest which of the FACS machines available to the user can be used. In either case, the wizard may then assist the user in scheduling an appropriate analysis time period on an appropriate FACS machine.

Finally, the protocol creator may use combinatorics or other procedures to define the reagent and cell sample combinations that the user may have to pipet (add to tubes) to complete the experiment and create a protocol for the researcher to follow. This protocol may specify the control tubes that are required and provide the concentrations and amounts of antibodies to use, the dilutions of the antibodies, the various steps to perform, the various centrifugations to perform, and the FACS to operate. Typically a control tube may be suggested for each antibody employed in the study. Further a blank control tube for each separate organism may be suggested to determine autofluorescence.

The reagents used by the protocol may have attributes associated with them. These attributes may include the reagent's distinguished name, Clone ID, Common name, Specificity, Titre, Fluorochrome Name, Fluorochrome Lot number, and concentration. The user may be prompted to select the reagents used through a "Reagent Palette". Such a palette may contain a catalog of reagents in stock, pre-determined sets of reagents typically used in similar protocols, and an ability for the user to enter a new choice of reagents for the experiment.

The protocol creator may also perform various tasks behind the scenes to create a valid protocol for the researcher, to call for pre-packaged analyses, to check data quality during data collection, and to display the information about the reagents and cells in a sample at the time of data collected or any other time.

The protocol editor may be tied to a database to enhance its, as well as the researcher's efficiency. In the previous example, several items may be used from the database to create the FACS protocol. For example, 1) The database may hold data for the fluorescent recognition abilities of all of the FACS machines available to the user. This may allow the protocol editor to select only those reagents that are available to the user and can be viewed by the FACS chosen by the user. There are a wide variety of possible combinations of possible reagent choices that can be selected. Specifically, there may be n!/(n-k)!k! possible reagent choices where n is the total number of fluorescent "colors" that for which the FACS can collect data and k is the number of stains used in the FACS experiment. However, this number is restricted because not all reagents are available in all colors.

The present invention may provide a novel way to enhance the effectiveness and speed of the selection of the reagent combination by applying well known combinatorial techniques and depth-first search in a new way to this biological problem. This may be performed by selecting one reagent at a time recursively. If the most recently added reagent cannot be used with the current set, then that reagent may be removed from the list of suggested reagents. The algorithm may run until a set of usable reagents is determined.

2) The protocol creator may also consult laboratory databases to determine how much of each reagent may be available to the user. If the protocol creator finds that the amount of reagent available is below a pre-set threshold, it may automatically indicate the reagent shortage and suggest another combination to be used. The protocol creator may also consult the database as to the effectiveness of each stain to bind to the type of cell being used. It may then use a greedy or any other algorithm (such as the ones suggested to select reagents combinations) to select an optimal set of stains to be used in the experiment. Other factors may also be taken into this optimization including the price of the reagents, the temperature compatibility of the reagents in a given combination, and the resolution possible for target cell surface or internal markers when stained with the selected reagent combination. This may be performed using a scoring function that provides a score for each of the factors in selecting the reagents.

3) The protocol creator may suggest the layout of the wells, tubes, or containers used to perform the experimental protocol. The layout may depend on the proximity of like samples, like reagents, and controls. The layout may also be created to minimize the movement of the person undertaking the protocol. Such an instance would be when several tubes require the same regent cocktail. In this case, it would be of benefit to have those wells, tubes, or containers located near one another. The protocol editor may also suggest the creation of reagent cocktails when several reagents with the same proportions are needed in various wells, tubes, and containers. The reagent cocktails may be designed by determination of like reagents used in multiple wells. This determination may be through linear programming or another optimization routine designed to minimize the number of pipeting steps or any other experimental concern such as time, cost, or ease. The constraints for such a linear programming model may include any of the aforementioned factors contributing to experimental time, ease, or cost.

4) The protocol creator may also suggest the use of different FACS machines that are capable of performing the experiment because either the FACS machine may be cheaper to operate or the cost of the reagents for that FACS machine may be cheaper. The protocol creator may also anticipate what type of data may be collected and may prepare table and charts to be filled in after the experimental data is collected. One method of creating charts may be to create 2-axes graphs for all the pairs of data that the protocol is expected to collect.

After a protocol is created and/or used, the protocol creator may then allow the user to store and re-use the protocol in the database under the current study or any other study the scientist wishes to use the protocol for. Once data collection for a sample is complete, the protocol creator may cooperate with the data collector to couple the collected data with the annotation information (reagents, cells, treatments) known to the creator and may send the coupled data and annotations to the database for permanent storage and archiving. Once the data collection for a full experiment is complete, experiment-related information (standards, machine conditions, etc) may be sent to the database to be coupled with the sample data and annotation. These couplings may be accomplished by storing the data separately from the annotation data and associating these items permanently by use of non-volatile pointers or some other means. The parent study may also be informed of the completion of the experiment and the location of the output from the experiment (protocol and data collection).

After the scientist creates the protocol, he is now able to perform the protocol and conduct the experiment. This experiment may create data that may automatically be captured by the database, coupled with the annotation information in the protocol, transferred from the machine used to collect the data (FACS, in the example above) directly to the proper location for the particular experimental data. This can be performed in several ways, including the use of LDAP, XML and XSL style sheets. Analysis programs may automatically perform preliminary analysis specified by the protocol or elsewhere. The protocol editor may determine the nature of data and may inform the analysis program the type of data that is represented. The data types may include nominal, ordinal, or continuous that are either dependant or independent variables. The variables may also be crossed or nested. These analyses may be informed by the annotation and possibly other information associated with the data (such as data type) collected for each sample. Results from these preliminary analysis may be stored and associated with the collected data and be locatable via an experiment data tree that may be available for the experimenter to view. For FACS analysis the collected and annotated data may automatically be sent to a FACS data analysis program such as FloJo or CellQuest. Once FACS analysis begins, the analysis software may suggest possible gating strategies with the use of clustering algorithms or other artificial intelligence techniques. Further gating data may be displayed using the annotations from the protocol editor to determine the labeling of the axes of the displayed data. The data also may be sent for analysis to a statistics analysis package such as JMP (from the SAS Institute). The data may be automatically processed to determine such statistics as median attribute values and standard deviations of attribute values.

As with any other scientific or engineering method, Gel electrophoresis may also be incorporated into the current system of protocol development. For instance, the protocol creation wizard may prompt the user to select/input the type of gel that is to be run. These gels may include a Northern or Southern blot. Further, the wizard may prompt the user to input the number of lanes in the gel and select the sample to be placed in each lane. The sample may be defined at the protocol level or may be selected from a list generated from information already entered into the study to which the experiment protocol belongs. Further, the protocol creation wizard, possibly informed by the study, may prompt the user to determine which type or types of standard controls, such as ladders, are going to be used in the experiment. The protocol wizard may suggest the lanes that each specimen should be placed in according to rules pre-defined for the type of gel and sample in the experiment.

After the experiment is completed, the user may bring the gel to an instrument for automated or manual data collection. For instance, the user may bring the gel to an ultra-violet gel reader connected to a computer. The reader may take a picture of the gel and send a digitized version, coupled with the protocol information that describes the sample and the experiment, to a central data store for archiving. The gel reader may then send the digitized picture to an analysis program. Alternatively, the data in the data store may be sent at the user's request, to the analysis program. This analysis program may determine the size of each fragment found in the gel by comparing their positions to the positions of the ladder. The results of the analysis may then be archived in the database for later retrieval, further analysis or abstraction into summaries in the parent study. The parent study may also be informed of the completion of the experiment and the location of the output from the experiment (protocol and data collection).

There are several experimental models which may be incorporated into the database. These models may be selected by the user to provide the protocol creator what type of experiment to create. The experimental models may include:

1) Crossing Model: Many experiments are essentially combinatorial, i.e., this set of reagents or reagent cocktails is applied to each sample in a group of samples. Typically it may correspond to some N×M grid of wells in the staining plate. An experiment might have 1 or more of these repeated sets of reagents.

2) Titration Model: The user may specify a target sample and a reagent and then a range of dilutions 2, 4, 8 . . . or 10, 20, 50, 100 being typical. The layout of the dilution may be as a single column, a single row, or otherwise on the plate or other type of container.

3) Screening Model: The user may specify a reagent cocktail and a large number of samples which are quasi-automatically named.

4) Fluorescence Compensation Controls Model: For each dye (or dye lot) which occurs in an experiment model, the user or protocol editor may specify a sample to be used as a control. Usually the control will be one of the samples which is stained with the reagent.

5) Unstained Controls Model: The user or protocol editor may define an unstained or negative control for a protocol involving staining. Unstained controls and fluorescence compensation-controls may be coupled in a together in a single experimental protocol to create a population of suitable controls.

The protocol editor may create a GUI representing the wells, tubes, or other containers holding the reagents and samples. The user may be able to "drag and drop" the sample or reagent to another well, tube, or container to alter the experimental protocol the user created or the protocol creator suggested.

After the study is completed the software may test the hypothesis stated in the study protocols. The hypothesis may be tested by combining the statistical information gathered during the experimental protocols and determining if they fit the hypothesis. This determination may be done manually by viewing the data or automatically by allowing the data to be analyzed by a data analysis package such as JMP. In one embodiment, JMP may automatically analyze the data that may be specified by the user when the user creates an experimental protocol with the appropriate wizard. The wizard may then associate the expected data with the study node so that the hypothesis may automatically be tested.

The database may allow access to the data for several purposes. First, the user may be able to provide hyperlinks to collected data and experimental protocols so that others may access the data and protocols. Others that would access the data may include collaborators, reviewers, and others reading published articles containing hyperlinks to the data. Second, the database may act as a cell surface expression library enabling people such as researchers and clinicians to facilitate diagnosis and definitions of new conditions by comparing the data from the database with locally collected data. Other uses of this database would be obvious to those skilled in the art.

The database may be constructed using any known database technique including the use of LDAP directories and protocols, XSLT style sheets, and XML documents. The database may be at a centralized site remote to the experimenter. The experimenter may send or receive information between his computer and the database via the Internet or any other communication means. LDAP is a "lightweight" (smaller amount of code) version of DAP (Directory Access Protocol), which is part of X.500, a standard for directory services in a network. The present invention may put these to unique uses in the scientific arena. In essence, the style-sheet transformation language (XSLT) defines the transformation of the original input (XML) document to "formatting objects" such as those included in HTML documents. In a traditional style sheet, these are then rendered for viewing. However, the XSLT transformation grammar can also be used to transform XML documents from one form to another, as in the following examples:

a) Loading directories. XSLT may be used to transform an XML file generated by any data processing application to an XML representation of a directory (sub)tree, i.e., to extracting directories entries from the XML document. The ability to use XSLT for this transformation greatly simplifies the creation and maintenance of LDAP or other directories that serve diverse information derived from distinct sources (e.g, FACS instruments and genome data banks) that generate different types of XML documents. In essence, using XSLT removes the necessity for writing distinct Java code to construct the directory entries for each type of document. Instead, appropriate "directory styles" can be defined for each document type and a single Java program can be written to process all XSL-transformed documents into the directory tree.

b) Re-indexing directory entries. Existing documents may be readily re-indexed based on any desired elements or attributes present in the XML documents simply by changing the XSLT style sheet. Changes in the directory schema may be required for extensive indexing changes but could also be driven by an XML representation of the appropriate schema.

c) Cataloging new documents. A new type of document can be cataloged simply by creating an appropriate XSLT style sheet and modifying the directory schema if necessary, as above.

d) Cataloging from arbitrary XML documents. A default XSLT directory style sheet can be created to extract a pre-defined set of indexing elements included in arbitrary XML documents. This would enable creation of the corresponding directory entries for these indexing elements.

e) Passing information from XML files to analytic or other programs: XSLT can be used to transform a subset of the information in an XML file so that it can be read by a program that takes XML input in a particular format. In addition, XSLT can launch the program and pass the result of the transformation during the launch. For example, using XSLT stylesheets, we can launch an analysis application by transforming an XML file containing the results of a directory search to an application-readable file containing URLs for the data and appropriate annotation information for the analysis. This option can be made available for all co-operating applications and need not be restricted to FACS data.

f) Creating data displays. XSLT style sheets can be used to change the form of a document. For example, they can be used to extract the results of analyses and display them as values in the rows or columns of a table.

As indicated above, XSLT and other capabilities may be used to store analysis output along with the primary data and annotation information. Alternatively, other developed fully cooperating applications may be used to analyze of FACS and other data.

A major advantage of LDAP is the availability of LDAP servers and client toolkits. Standalone servers and LDAP to X.500 gateways are available from several sources. LDAP client libraries are available for the C language from Univ. Michigan and Netscape and for the Java language from Sun and Netscape.

Secondly, LDAP is a standard that is directly utilized by the clients and makes it possible for all clients to talk to all servers. In contrast, SQL standardization may be more apt with transportability of programmers and database schema than interoperability of databases.

The X.500 information model is extremely flexible and its search filters provide a powerful mechanism for selecting entries, at least as powerful as SQL and probably more powerful than typical OODB. The standard defines an extensibleObject that can have any attribute. Furthermore, some stand-alone LDAP implementations permit relaxed schema checking, which in effect makes any object extensible. Since an attribute value may be a distinguished name, directory entries can make arbitrary references to one another, i.e., across branches of the directory hierarchy or between directories.

Finally, some LDAP and X.500 servers permit fine grained access control. That is to say, access controls can be placed on individual entries, whole sub trees (including the directory itself) and even individual attributes if necessary. This level of control is not available in most existing databases.

One example of an LDAP directory is organized in a simple "tree" hierarchy consisting of the following levels:

1) The "root" directory (the starting place or the source of the tree), which branches out to 2) Countries, each of which branches out to 3) Organizations, which branch out to 4) Organizational units (divisions, departments, and so forth), which branches out to (includes an entry for)

5) Individuals (which includes people, files, and shared resources such as printers)

Figure 1:
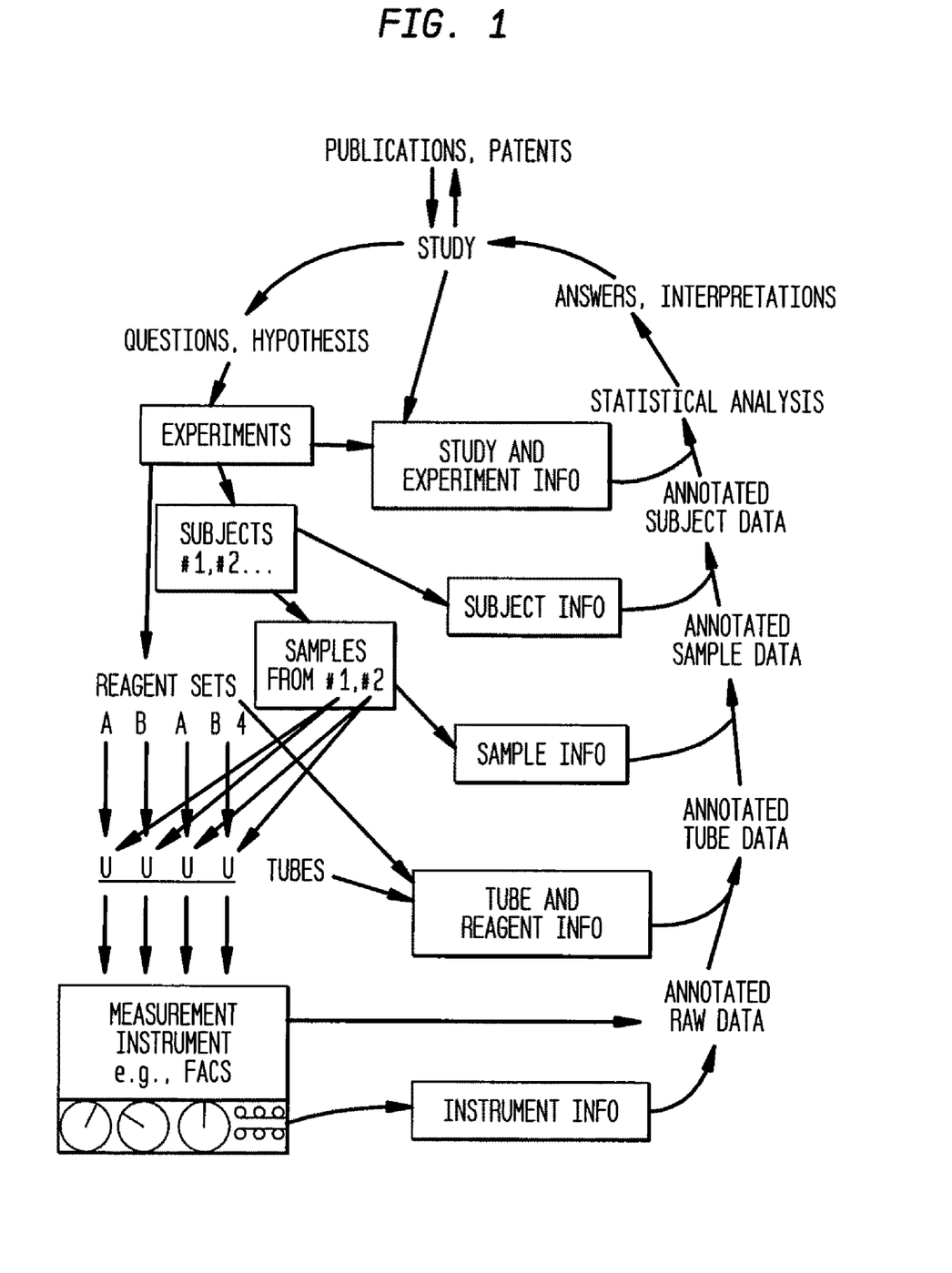
FIG. 1 is a diagram of the flow of information in a biological experiment.
Figure 2:
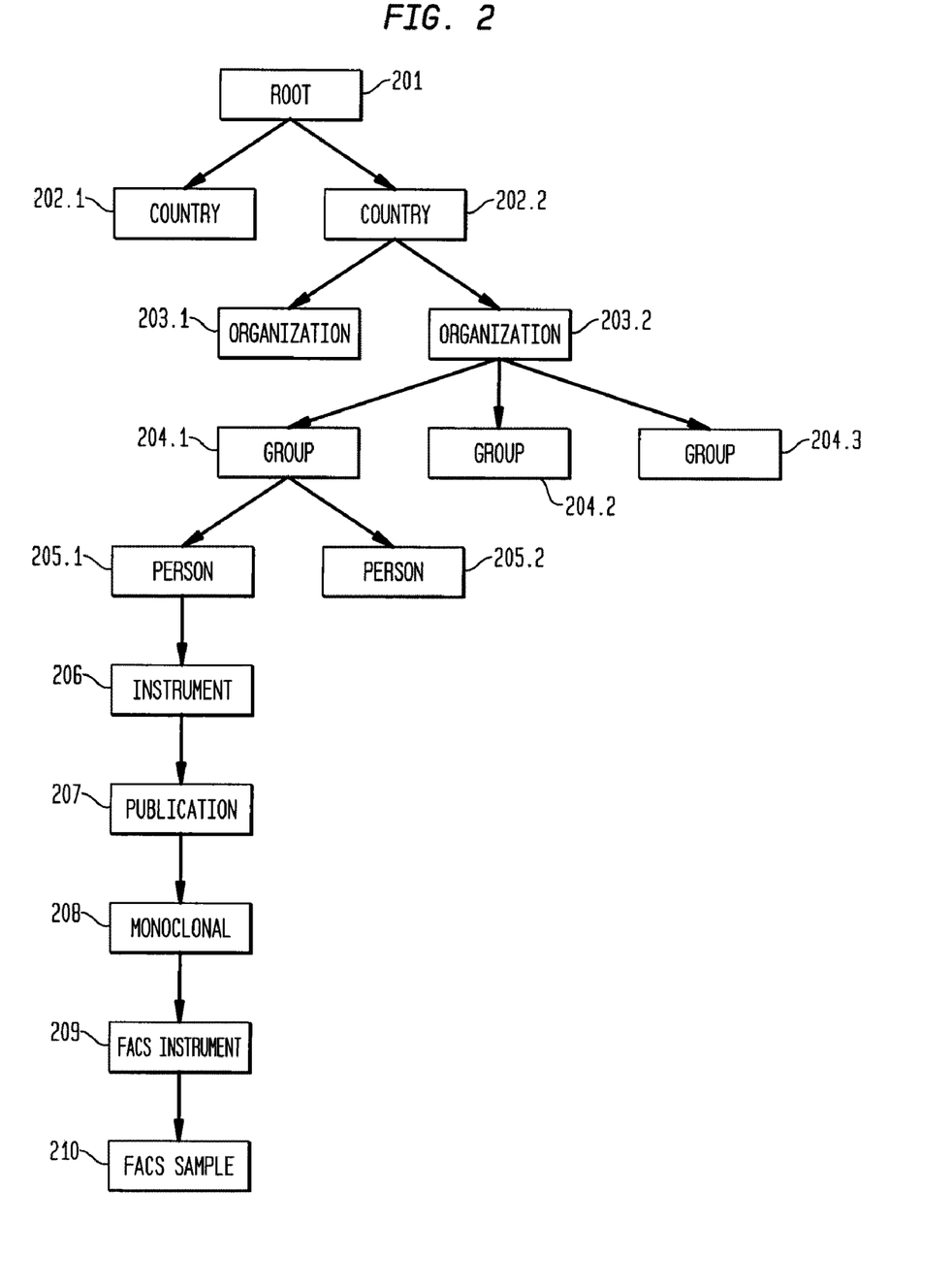
FIG. 2 is a diagram of a directory archival system.
Figure 3:
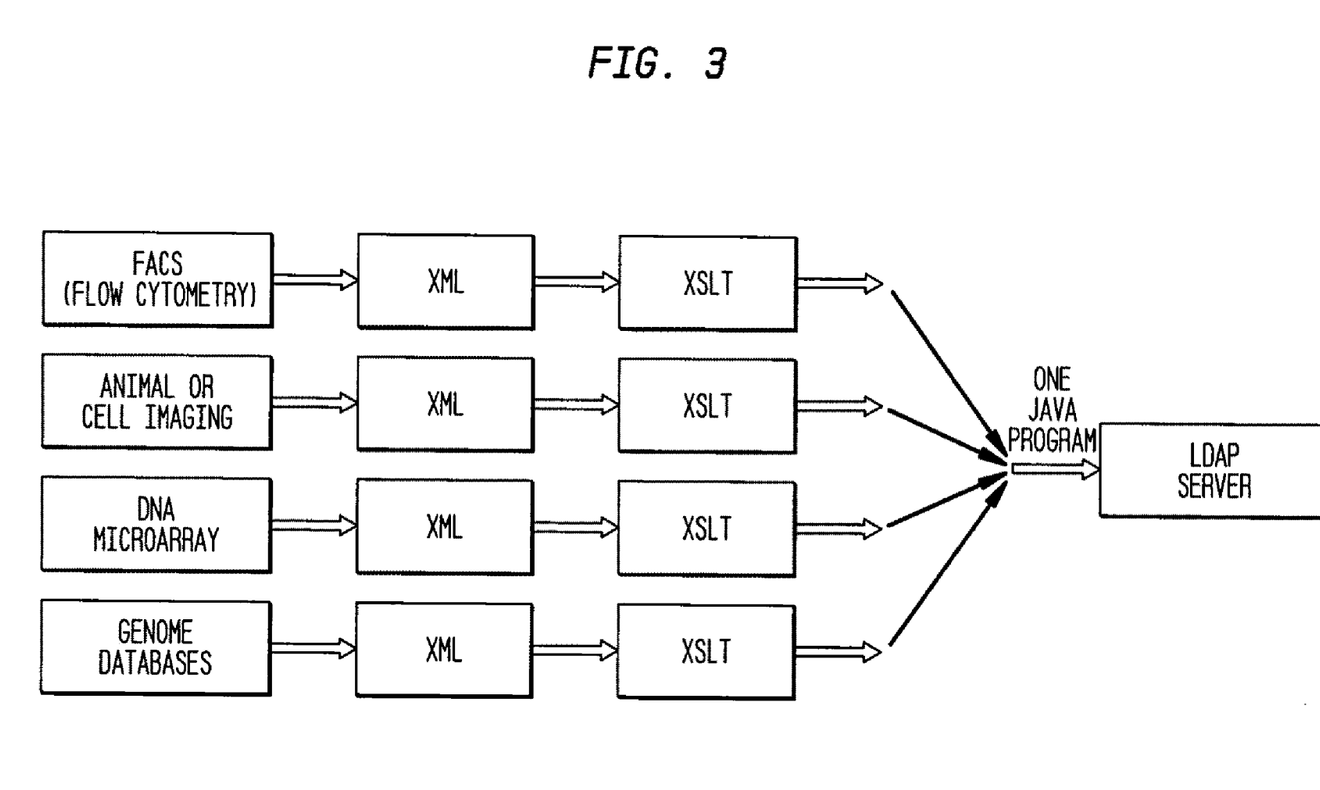
FIG. 3 is a diagram of information flow from instruments to and from the database (IBRSS) in one embodiment of the present invention.
Figure 4:
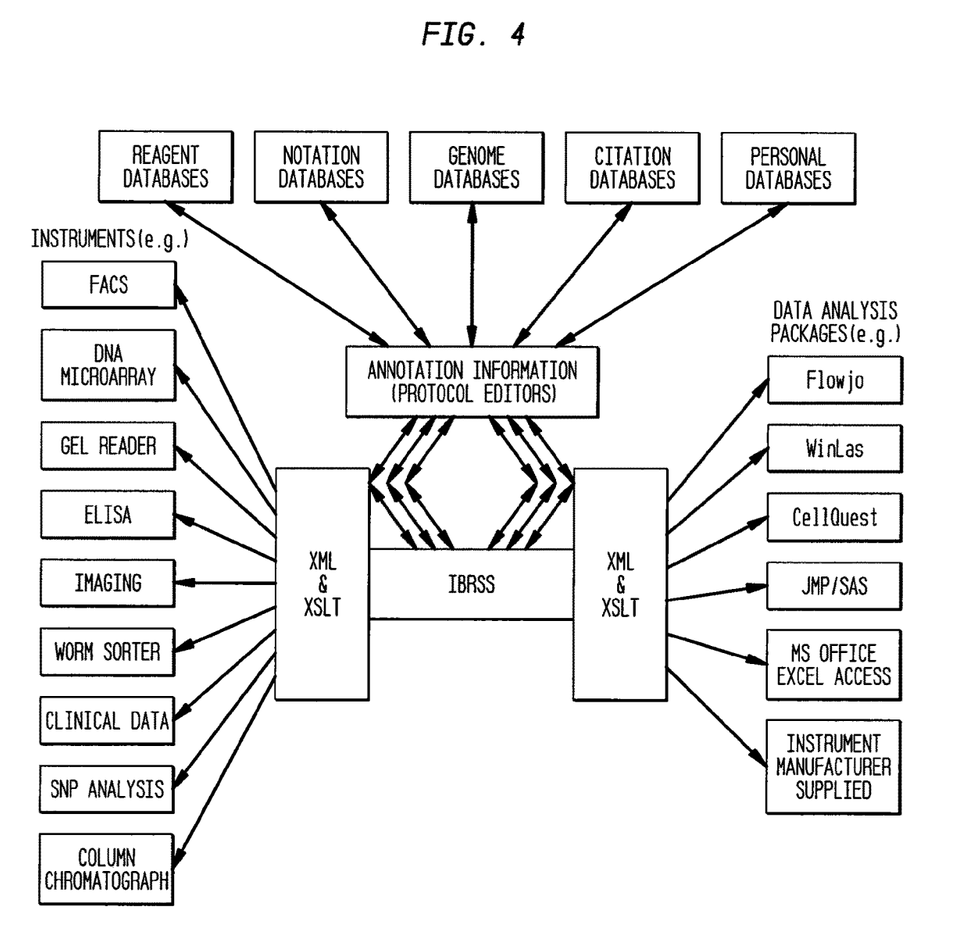
FIG. 4 is a diagram of information flow from instruments, analysis programs, remote databases, and other software and to the central database in one embodiment of the present invention.

This example tree structure of an LDAP directory is illustrated in FIG. 2. The parent node of the tree is the root node 201. The children of the root directory are country nodes 202.1 and 202.2. Each country node can have child organization nodes such as organization nodes 203.1 and 203.2 (children of country node 202.2).

Below the organization level are organization group nodes such as nodes 204.1, 204.2, and 204.3, which are children of organization node 203.2. Each group can have children nodes representing individuals such as group node 204.1 having children nodes 205.1 and 205.2.

In a network, a directory tells you where in the network something is located. On TCP/IP networks (including the Internet), the Domain Name System (DNS) is the directory system used to relate the domain name to a specific network address (a unique location on the network). However, sometimes the domain name is not known. There, LDAP makes it possible to search for an individual without knowing the domain.

An LDAP directory can be distributed among many servers. Each server can have a replicated version of the total directory that is synchronized periodically. An LDAP server is called a Directory System Agent (DSA). An LDAP server that receives a request from a user takes responsibility for the request, passing it to other DSAs as necessary, but ensuring a single coordinated response for the user.

The present invention contemplates extensions and modifications to LDAP protocols to make them usable not just as directories, but to also provide data itself. The present invention takes advantage of hierarchical levels of LDAP already established by the International Standards Organization (ISO) and uses those organizations to provide a first level of uniqueness to the biological sample to be named.

Referrals mean that one server which cannot resolve a request may refer the user to another server or servers which may be able to do so. During a search operation any referrals encountered are returned with the entries located and the user (or client) has the option of continuing the search on the servers indicated. This allows federation of directories which means that multiple LDAP/X.500 servers can present to the user a unified namespace and search results even though they are at widely separated locations and the implementations may actually be very different.

The Java Naming and Directory Interface (JNDI) is a standard extension to the Java language introduced Java Naming and Directory Interface by Sun. It includes an abstract implementation of name construction and parsing that encompasses the X.500 name space (among others), and an abstract directory that is essentially the X.500 information and functional models. Specific implementations (service providers[13]) are available for LDAP, Network Information Server (NIS) and even the computers own file system.

JNDI may remove many of the limitations of LDAP as an OODB by providing a standard way to identify the Java class corresponding to a directory entity and instantiate it at runtime. It also allows storage of serialized Java objects as attribute values. Sun has proposed a set of standard attributes and objectClasses to do this.

When represented as a string (essentially always with LDAP) an X.500 distinguished name is a comma separated list of attribute value pairs and is read from right to left. If a value contains special characters such as commas it must be quoted and in any case initial and final white space around attributes or values is ignored. For example, "cn=Wayne Moore, ou=Genetics Department, o=Stanford University".

Location names may have as their root (right most) component the countryName or c attribute with the value being one of the ISO standard two letter country codes, for example c=US. Such names can be further restricted by specifying a stateOrProvinceName abbreviated st and a locality abbreviated l, for example "l=San Francisco, st=California, c=US".

Organizational names may have as their root the name (registered with ISO) of a recognized organization and may be further qualified with one or more organizational units, for example "ou=Department of Genetics, ou=School of Medicine, o=Stanford University".

Domain names as used by the Domain Name Service (DNS) are represented with the dc attribute, for example, "dc=Darwin, dc=Stanford, dc=EDU".

Names of persons. There are two conventions for naming people. The older uses the commonName or cn attribute of the Person objectClass but these are not necessarily unique. Some directories use the userId or UID attribute of inetOrgPerson, which is unique. Since uniqueness is important for scientific applications the latter may be used. The remainder of a person's dn is usually either an organizational or geographic name, for example "uid=wmoore, o=Stanford University" or "cn=Wayne Moore, l=San Francisco, st=California, c=US".

Examples of encapsulating and extending existing nomenclatures:

1. Gene loci, for example, "locus=Igh-1, o=Professional Society or locus=New, cn=Leonard Herzenberg, ou=Department of Genetics, ou=School of Medicine, o=Stanford University".
2. Gene alleles, for example, "allele=a, locus=Igh-1, o=Professional Society or allele=1, locus=127, ou=Department of Genetics, o=Stanford University".
3. CD antigens, for example, "specificity=CD23, o=Human Leukocyte Differentiation Workshop".
4. Literature references in the scientific literature are essentially achieved the benefits of distinguished names without an explicit central authority. However representing them as distinguished names may facilitate mechanical processing. For example, "title="A Directory of Biological Materials", volume=1999, o="Pacific Symposium on Biocomputing". A true directory of such literature references would be of obvious value over and above the current unique naming systems in some of the current literature archives.
5. New nomenclature schema. The following schemas arose from work on storing information about flow cytometry data in directories.
6. Monoclonal antibodies are distinguished by cloneName or clone which is unique within the parent entity which must be an investigator or organization.
7. Lymphocyte differentiation antigens, a thesaurus of the target specificities of monoclonal antibodies. Would include but not be limited to the official CD names.

8. FACS instruments are distinguished by the cytometer attribute which must be unique with respect to the organization parent, for example, "cytometer=Flasher II, ou=Shared FACS Facility, o=Stanford University".
9. FACS experiments are distinguished by the protocolIdentifier or protocol attribute which must be unique with respect to the parent which may be a person, and instrument or and organization or some combination, e.g., "protocol=1234, cytometer=Flasher, uid=Moore, ou=Shared FACS Facility, o=Stanford University".
10. FACS samples are distinguished by a unique protocolCoordinate which must be unique within the parent FACS experiment, e.g., "coord=A12a, protocol=12345, cytometer=Mollusk, ou=Shared FACS Facility, o=Stanford University".

Therefore, using LDAP any object, such as a monoclonal antibody, may be named relative to the unique distinguished name of an investigator or organization. That means that unique identifiers can be assigned to biological materials early in the scientific process and thus facilitate professional communication both informal and published. In the future, investigators who have this distinguished name can identify the material unambiguously via the unique name. If a directory services is maintained, an investigator can determine if the sample has been given an official name, if it has been shown to be equivalent to another entity or if it has been cited in the literature.

Directory searches may also be a tool available in the database. Information may be promoted upward from the documents into the directory for searching and no searching is done within the documents. However, since XQL or Xpath allows searches to proceed downwards from the directory, a search application may use the LDAP search functions to retrieve a set of candidate XML documents (based on their directory attributes) and then may use XQL or Xpath to further refine this set. To facilitate XQL or Xpath use, a unified interface may be provided that would largely make the differences in search strategies transparent to the user. The user then may be able to select (search and retrieve) for items within the document that are not reflected in the directory or may extract elements from these documents, e.g., samples from a set of experiments.

The instruments may be responsible to collect, annotate and export the collected experimental data. The instruments may annotate it with information generated during the data collection, and may transmit the annotated primary data to the LDAP server for storage in the database in association with the appropriate XML-encoded experiment and study descriptions. The following modules may be used to perform these functions:
 a) Set-up module(s)—automate aspects of instrument set-up and standardization; record and visualize relevant instrument information; acquire and respond to user input
 b) Data collection module(s)—collect primary (instrument-generated) data for the aliquots of each sample; visualize protocol information to facilitate data collection; acquire and respond to user input; record machine condition and user comments specific to each data collection.
  i) adapt and interface the data collection modules to specific machines (e.g., various FACS, imaging and DNA-array data readers) to provide full functionality for data collection.
  ii) For instruments that do not provide/permit direct access to machine control and data collection, use additional modules that may enable manual entry of machine information and "point-and-click" association of primary data collected for each sample aliquot with the protocol information for that aliquot.
 c) Extension of the FACS document type—include new functionality such as instrument setup, auto-calibrator and quality control elements, tabulated transfer functions and operator commentary in the definitions of the FACS document type. Provisions for digests of the data files that are referenced and for digital signatures may also be made.
 d) Data transmission module(s)—link (annotate) the primary data with protocol instrument-derived information; communicate authenticated (digitally-signed) primary data and its annotation linkages to the information store.

The central database may be a large scale (terabyte level), web accessible, central storage system coupled with small-scale volatile storage deployed locally in a manner transparent to the user. This system may store data and annotation information transmitted from the data collection system. In addition, it may catalog the stored data according to selected elements of the structured annotation information and may retain all catalog and annotation information in a searchable format. Wherever possible, industry standard formats for storing data and annotation information will be implemented. If no standard is available, interim formats may be used and may allow for translators to industry standards once the industry standards become available.

The database may capitalize on the built-in replication and referral mechanisms that allow search and retrieval from federated LDAP networks in which information can be automatically replicated, distributed, updated and maintained at strategic locations throughout the Internet. Similarly, because pointers to raw data in LDAP are URLs to data store(s), the database may capitalize on the flexibility of this pointer system to enable both local and central data storage.

The database may enable highly flexible, owner-specified "fine-grained" access controls that prevent unauthorized access to sensitive information, facilitate sharing of data among research groups without permitting access to sensitive information, and permit easy global access to non-sensitive data and analysis results.
 a) Built-in access controls that may prevent release of unauthorized information from the system
 b) Multi-level access controls that may allow data owners to specify which users, or classes of users, are permitted to retrieve individual data sets and/or to access individual elements of the annotation information during searches
 c) User identity verification system that may be referenced by the access control system
 d) Anonymous access to data and annotation information that owners may make available for this purpose
 e) Security and encryption may be implemented to protect the information in the database itself as well in the communications between the central data repository and the remote locations.

The central database may also allow for the retrieval of annotated data sets (subject to owner-defined accessibility) via catalog browsing and/or structured searches of the catalog. The central database may also automatically verify authenticity of the data based on the data's digital signature. This function may be accomplished by launching internal and co-operating data analysis and visualization programs and transferring the data and annotation information to the program. Further the database may put the data and annotation information into published-format files that can be imported into data analysis and visualization programs that do not provide launchable interfaces.

The central database may also allow for retrieval of analysis output. This function may be accomplished by recovering/importing the link analysis output with primary and annotation data to provide access to findings via subject and treatment information that was entered at the study and experiment levels. This may allow the database to store and catalog output from co-operating analysis programs (within the limitations imposed by the capabilities of analysis programs that were not designed for this purpose). It may also allow the database to use internal analytic modules and programs that may enable users to fully capitalize on the annotation information entered into the system. This specification also incorporates by reference "*A Directory of Biological Materials*" by Wayne Moore and "*Grant proposal for the IBRSS system*".

What is claimed is:

1. A method for extending and managing a database for an assay by identifying and storing annotation information gathered during planning of an experiment with said database, said method comprising the steps of:
   (a) creating a directory structure for said database, said directory structure having a plurality of nodes with names;
   (b) annotating experiment-data to form standardized experiment-data annotation information,
   wherein the annotating step further comprises the steps of:
      (i) collecting, by a computer, said standardized experiment-data annotation information, and
      (ii) transmitting, by the computer, said standardized experiment-data annotation information into said database as part of development of an experiment plan before data collection, wherein said standardized experiment-data annotation information is made available for combination with assay data during data collection; and
   (c) exporting, by the computer, the standardized experiment-data annotation information to a cooperating instrument for viewing during data collection and for combining with the assay data for subsequent use,
   wherein the step of annotating experiment-data occurs during development of an experiment plan.

2. The method of claim 1, wherein said creating step further comprises:
   (a) developing extensions with XML; and
   (b) mapping said extensions to said plurality of nodes.

3. The method of claim 2, wherein said developing step further comprises adding to said extensions, elements selected from the group consisting of cross-references, external pointers and links.

4. The method of claim 1, further comprising a centralized Internet-accessible archive for storing, analyzing, retrieving, and sharing said experiment-data.

5. The method of claim 1, further comprising a security means for user-controlled sharing of the experiment-data.

6. The method of claim 1, further comprising a structured hierarchy for said experiment-data, said structured hierarchy comprising, in order:
   (a) studies;
   (b) experiments;
   (c) data; and
   (d) analysis.

7. The method of claim 1, wherein the experiment-data further includes measurement data.

* * * * *